United States Patent
Schlomka et al.

(10) Patent No.: US 7,551,709 B2
(45) Date of Patent: Jun. 23, 2009

(54) FAN-BEAM COHERENT-SCATTER COMPUTER TOMOGRAPHY

(75) Inventors: Jens-Peter Schlomka, Hamburg (DE); Geoffrey Harding, Hamburg (DE)

(73) Assignee: Koninklijke Philips Electrions N.V., Eindhoven (NL)

( * ) Notice: Subject to any disclaimer, the term of this patent is extended or adjusted under 35 U.S.C. 154(b) by 102 days.

(21) Appl. No.: 10/557,688

(22) PCT Filed: May 18, 2004

(86) PCT No.: PCT/IB2004/050733

§ 371 (c)(1),
(2), (4) Date: Jan. 9, 2007

(87) PCT Pub. No.: WO2004/105610

PCT Pub. Date: Dec. 9, 2004

(65) Prior Publication Data

US 2007/0172026 A1    Jul. 26, 2007

(30) Foreign Application Priority Data

May 28, 2003    (EP) .................................. 03101557

(51) Int. Cl.
*A61B 6/03*    (2006.01)
(52) U.S. Cl. ................... 378/6; 378/57; 378/87
(58) Field of Classification Search ............... 378/6, 378/19, 57, 87, 88
See application file for complete search history.

(56) References Cited

U.S. PATENT DOCUMENTS

| 4,751,722 A | 6/1988 | Harding et al. |
| 4,754,469 A | 6/1988 | Harding et al. |
| 5,008,911 A | 4/1991 | Harding |
| 5,696,806 A * | 12/1997 | Grodzins et al. ............. 378/86 |
| 5,901,198 A * | 5/1999 | Crawford et al. ............. 378/57 |
| 6,246,743 B1 * | 6/2001 | Kopp et al. ................... 378/19 |
| 6,470,067 B1 | 10/2002 | Harding |

(Continued)

FOREIGN PATENT DOCUMENTS

DE    10252662 A1    5/2004

(Continued)

OTHER PUBLICATIONS

Schlomka et al., "Coherent scatter X-ray computed tomography in medical applications", Nuclear Science Symposium Conference Record, 2002 IEEE, vol. 2, Nov. 2002, pp. 900-901.*

(Continued)

*Primary Examiner*—Chih-Cheng G Kao

(57) ABSTRACT

In CSCT, by using a fan-shaped primary beam, combined with a 2D detector, single-slice transmission tomography and scatter tomography can be measured simultaneously. In such a System blurred scatter functions are measured unless a monochromatic source of radiation is used. According to the present invention, an energy resolving 1D or 2D detector System is proposed, which, in combination with a tomographic reconstruction, provides a good spectral resolution, even with a polychromatic primary beam. Furthermore, according to an aspect of the present invention, only one energy resolving detector-line is required to achieve the fall spectrum. Advantageous applications of the system and method according to the present invention are in medical imaging and material analysis, such as baggage inspection.

8 Claims, 7 Drawing Sheets

U.S. PATENT DOCUMENTS

2002/0150202 A1 * 10/2002 Harding et al. ............... 378/16

FOREIGN PATENT DOCUMENTS

| WO | 9833062 A1 | 7/1998 |
| WO | 02082065 A2 | 10/2002 |

OTHER PUBLICATIONS

Schneider et al, "Coherent Scatter Computer Tomography Applying a Fan-Beam Geometry", Proc. SPIE, 2001, vol. 4320, pp. 754-763.

Harding et al, "Energy-dispersive x-ray Diffraction Tomography", Phys. Mid. Biol., 1990, vol. 35, No. 1, pp. 33-41.

Schlomka et al, "Coherent Scatter X-ray Computed Tomography in Medical Applications", IEEE, 2003, Philips Research Laboratories, Hamburg, Germany, pp. 900-901.

* cited by examiner

FAN-BEAM COHERENT-SCATTER COMPUTER TOMOGRAPHY

The present invention relates to the fields of coherent-scatter computer tomography (CSCT) where a fan-beam is applied to an object of interest. In particular, the present invention relates to a computer tomography apparatus for examination of an object of interest and to a method of examining an object of interest with a computer tomography apparatus.

U.S. Pat. No. 4,751,722 describes a device based on the principle of registration of an angled distribution of coherent scattered radiation within angles of 1° to 12° as related to the direction of the beam. As set forth in the U.S. Pat. No. 4,751,722, the main fraction of elastic scattered radiation is concentrated within angles of less than 12°, and the scattered radiation has a characteristic angle dependency with well marked maximas, the positions of which are determined by the irradiated substance itself. As the distribution of the intensity of the coherently scattered radiation in small angles depends on molecular structure of the substance, different substances having equal absorption capacity (which cannot be differentiated with conventional transillumination or CT) can be distinguished according to the distribution of the intensity of the angled scattering of coherent radiation typical for each substance.

Due to the improved capabilities of such systems to distinguish different object materials, such systems find more and more application in medical or industrial fields.

The dominant component of low-angle scatter is coherent scatter. Because coherent scatter exhibits interference effects which depend on the atomic arrangement of the scattering sample, coherent scatter computed tomography (CSCT) is in principle a sensitive technique for imaging spatial variations in the molecular structure of tissues across a 2D object section.

Harding et al "Energy-dispersive x-ray diffraction tomography" Phys. Med. Biol., 1990, Vol. 35, No. 1, 33-41 describes an energy dispersive x-ray diffraction tomograph (EXDT) which is a tomographic imaging technique based on an energy analysis at fixed angle, of coherent x-ray scatter excited in an object by polychromatic radiation. According to this method, a radiation beam is created by the use of suitable aperture systems, which has the form of a pencil and thus is also referred to as a pencil beam. Opposite to the pencil beam source, one detector element suitable for an energy analysis is arranged for detecting the pencil beam altered by the object of interest.

Due to the use of the pencil beam in combination with only one detector element, only a limited number of photons emitted by the source of radiation and thus only a reduced amount of information can be measured. In case EXDT is applied to larger objects such as for example to pieces of baggage, EXDT has to be used in a scanning mode thus causing extremely long measurement times.

A coherent scatter set-up applying a Fan-beam primary beam and a 2D detector in combination with CT was described in U.S. Pat. No. 6,470,067 B1 thus overcoming the long measurement time involved in EXDT scanning mode. The shortcoming of the angle-dispersive set-up in combination with a polychromatic source are blurred scatter functions, which is described in e.g. Schneider et al. "Coherent Scatter Computed Tomography Applying a Fan-Beam Geometry" Proc. SPIE, 2001, Vol. 4320 754-763.

It is an object of the present invention to provide for an improved material discrimination on the basis of computer tomography.

According to and exemplary embodiment of the present invention, the above object may be solved with a computer tomograph apparatus for examination of an object of interest, which comprises a detector unit with an x-ray source and a scatter radiation detector. The detector unit is rotatable around a rotation axis extending through an examination area for receiving the object of interest. The x-ray source generates a fan-shaped x-ray beam adapted to penetrate the object of interest in the examination area in a slice plane. The scatter radiation detector is arranged at the detector unit opposite to the x-ray source with an offset from the slice plane in a direction parallel to the rotational axis. The scatter radiation detector includes a first detector line, with a plurality of first detector elements arranged in a line. According to an aspect of the present invention, these first detector elements are energy-resolving detector elements. Preferably, the energy resolving detector elements are direct-converting semiconductor detectors. Direct-converting semiconductor detectors directly convert the radiation into electrical charges—without scintillation. Preferably, these direct-converting semiconductor detectors have an energy resolution better than 20% FWHM, i.e. $\Delta E/E < 0.2$, with $\Delta E$ being the Full-width at half maximum (FWHM) of the energy resolution of the detector. The scatter radiation detector measures a spectrum (I) for each projection which is the intensity I depending on the energy E of photons. Advantageously, this spectrum may then be used for the tomograph reconstruction, as for example with ART (Algebraic Reconstruction Technique) or FBP (Filtered Back-Projection).

Advantageously, the computer tomograph apparatus according to this exemplary embodiment allows to significantly reduce a scanning or measurement time in comparison to the apparatus suggested by Harding et al in U.S. Pat. No. 4,751,722, since an energy resolving detector line including a plurality of energy resolving detector elements is applied in combination with a fan-beam, which allows an integral measurement of the line at the same time. In other words, a whole projection of the object of interest along the slice plane is measured at the same time. While significantly reducing the time required for measurements, according to this exemplary embodiment of the present invention, an improved characterization of tissue of the object of interest is made possible since an increased amount of photons emitted by the source of radiation are detected and thus more information with respect to the tissue is detected. In contrast to U.S. Pat. No. 6,470,067, the use of energy-resolving detectors allows a better resolution of the coherent scatter structure function when using a polychromatic source.

According to another exemplary embodiment of the present invention, besides the scatter radiation detector, which is arranged at the detector unit outside the slice plane, a primary radiation detector is provided for receiving primary radiation attenuated by the object of interest. In other words, two radiation detectors are provided, one for detecting the scatter radiation and one for detecting the primary radiation. Advantageously, this may provide for a further improvement with respect to the material discrimination and identification due to improved attenuation correction of the scattered radiation.

According to another exemplary embodiment of the present invention, the energy resolving elements are direct-conversion semiconductor cells, eg. CdZnTe or cadmiumtelluride cells and the primary radiation detector includes a detector line with a plurality of scintillator cells. According to this exemplary embodiment of the present invention, the primary radiation detector detects the attenuation of the primary radiation in the slice plane. Advantageously, the attenuation of the primary beam is used to improve the quality of the reconstruction of the scatter data I(E) as described by Schneider et al.

According to another exemplary embodiment of the present invention, at least one of a plurality of first detector lines for the energy resolving measurement of the scatter radiation and a plurality of second detector lines for the measurement of the primary radiation attenuated by the object of interest are provided. Advantageously, this may further reduce the scanning time required for scanning the object of interest. Furthermore, according to this exemplary embodiment of the present invention, at least one of the primary radiation detector and the scatter radiation detector is provided with collimator elements such as lamella or blades, which avoids that the respective detector elements measure unwanted dispersed radiation.

According to another exemplary embodiment of the present invention, there is provided a calculation unit for reconstructing an image from readouts of the primary radiation detector and the scatter radiation detector, by, as already mentioned above, for example ART or a filtered back projection. Furthermore, the computer tomograph apparatus may also be adapted for the detection of explosives, for example for the application as x-ray baggage inspection system at airports, which automatically discriminates explosive materials on the basis of the reconstructed coherent scatter function images based on readouts of the primary radiation detector and the scatter radiation detector by, for example, comparing the reconstructed scatter functions to predetermined tables of characteristic measurements for such explosives.

According to another exemplary embodiment of the present invention, the above object may also be solved with a method of examining an object of interest with a computer tomograph apparatus, wherein an x-ray source is energized, such that it generates a fan-shaped x-ray beam, which penetrates the object of interest in an examination area in a slice plane. Then, a measurement of the scattered radiation is performed by means of a scatter radiation detector with a first detector line with a plurality of first energy resolving detector elements arranged in a line. The energy-resolved intensity I(E) from the scatter radiation detector is read out. For acquiring a plurality of projections of the object of interest, the x-ray source and the scatter radiation detector are rotated around a rotational axis extending through an examination area containing the object of interest.

Advantageously, according to this exemplary embodiment of the present invention in combination with a suited reconstruction method, a method may be provided which allows for a fast and dependable material discrimination of the object of interest.

According to another exemplary embodiment of the present invention, a primary radiation attenuated by the object of interest is read out.

According to another exemplary embodiment of the present invention, an image is reconstructed from the readouts of the primary radiation detector and the scatter radiation detector, for example by ART or a filtered back projection technique. Furthermore, according to this exemplary embodiment of the present invention, an automatic determination may be carried out on the basis of the readouts of the primary radiation detector and the scatter radiation detector, whether the object of interest comprises explosives or not. In case it is determined that the object of interest contains explosives, an alarm may be issued.

According to another exemplary embodiment of the present invention, the readouts of a plurality of lines of the scatter radiation detector or a plurality of lines of the primary radiation detector is performed and a collimation of the respective radiation is carried out, which may allow to further improve the material discrimination.

It may be seen as the gist of an exemplary embodiment of the present invention that an image reconstruction is performed or a material discrimination is performed by using measurements of an energy spectrum of photons scattered from a fan-beam by an object of interest which are measured by means of a detector line including energy resolving detector elements. An improved material discrimination may be provided by further using the attenuation of the primary beam of the fan-beam measured by means of, for example, a line of scintillator elements in the slice plane.

These and other aspects of the present invention will become apparent from and elucidated with reference to the embodiments described hereinafter.

Exemplary embodiments of the present invention will be described in the following with reference to the following drawings.

Figure 1:
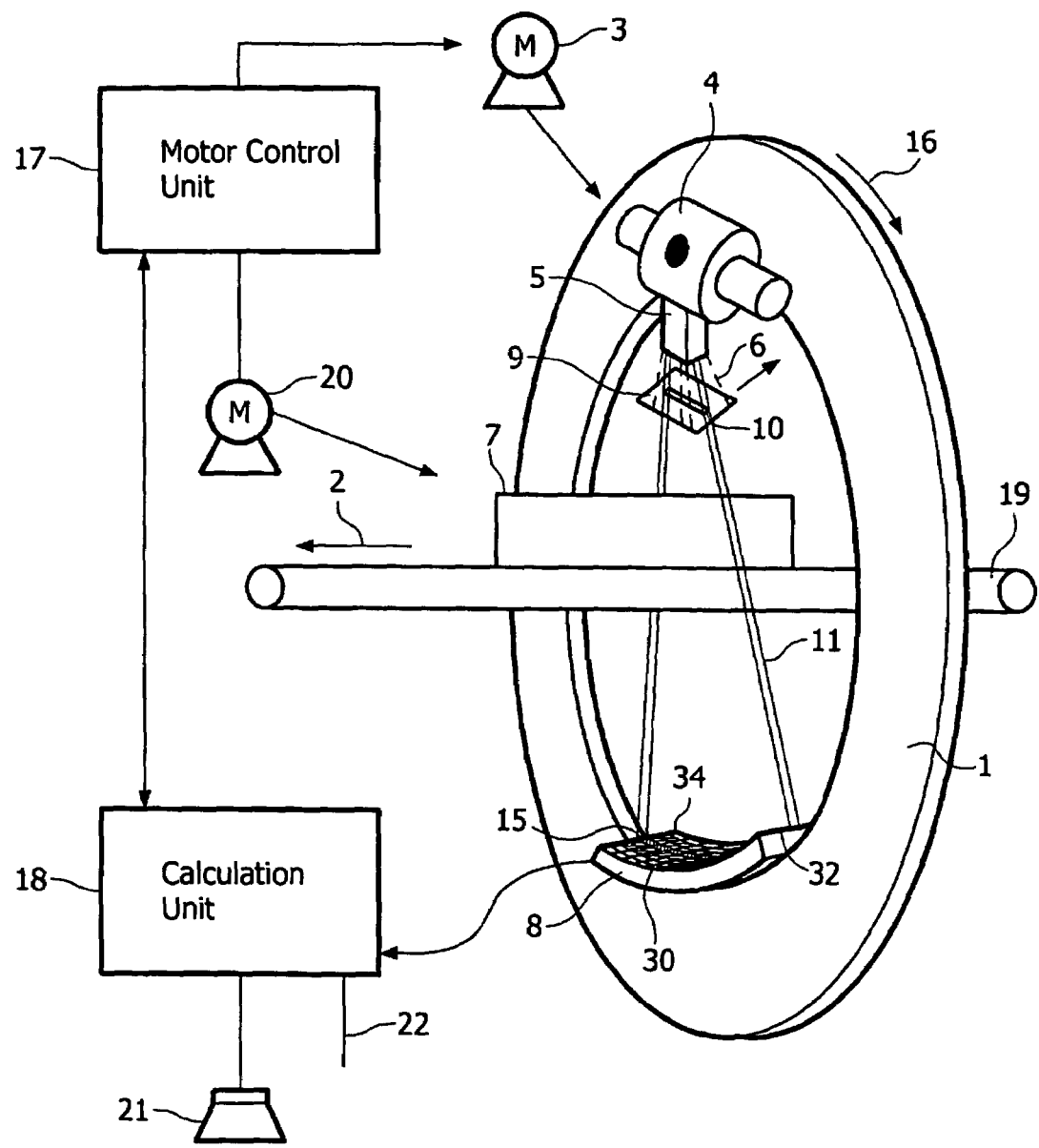
FIG. 1 shows a schematic representation of an exemplary embodiment of a computer tomograph according to the present invention.

FIG. 1 shows an exemplary embodiment of computer tomograph according to the present invention. With reference to this exemplary embodiment, the present invention will be described for the application in baggage inspection to detect hazardous materials such as explosives in items of baggage. However, it has to be noted that the present invention is not limited to applications in the field of baggage inspection, but can also be used in other industrial or medical applications, such as for example in bone imaging or a discrimination of tissue types in medical applications.

The computer tomograph depicted in FIG. 1 is a fan-beam coherent scatter computer tomograph (CSCT), which allows in combination with an energy-resolving detector and with tomographic reconstruction a good spectral resolution, even with a polychromatic primary fan-beam. The computer tomograph depicted in FIG. 1 comprises a gantry 1, which is rotatable around a rotational axis 2. The gantry 1 is driven by means of a motor 3. Reference character 4 designates a source of radiation, such as an x-ray source, which, according to and aspect of the present invention, emits a polychromatic radiation.

Reference character 5 designates a first aperture system, which forms the radiation beam emitted from the radiation source 4 to a cone shaped radiation beam 6. Furthermore, there is provided another aperture system 9 consisting of a diaphragm or a slit collimator. The aperture system 9 has the form of a slit 10, such that the radiation emitted from the source of radiation 4 is formed into a fan-beam 11. According to a variant of this exemplary embodiment of the present invention, the first aperture system 5 may also be omitted and only the second aperture 9 may be provided.

The fan-beam 11 is directed such that it penetrates the item of baggage 7, arranged in the center of the gantry 1, i.e. in an examination region of the computer tomograph and impinges onto the detector 8. As may be taken from FIG. 1, the detector 8 is arranged on the gantry 1 opposite to the radiation source 4, such that the slice plane of the fan-beam 11 intersects a row or line 15 of the detector 8. The detector 8 depicted in FIG. 1 has seven detector lines, each comprising a plurality of detector elements. As mentioned above, the detector 8 is arranged such that the primary radiation detector 15, i.e. the middle line of the detector 8 is in the slice plane of the fan-beam 11.

As can be taken from FIG. 1, the detector 8 comprises two types of radiation detector lines: a first type of detector lines 30 and 34, which are indicated without hatching in FIG. 1, which are detector lines consisting of energy resolving detector cells. According to an aspect of the present invention, these first detector elements (lines 30 and 34) are energy-resolving detector elements. Preferably, the energy resolving detector elements are direct-converting semiconductor detectors. Direct-converting semiconductor detectors directly convert the radiation into electrical charges—without scintillation. Preferably, these direct-converting semiconductor detectors have an energy resolution better than 20% FWHM, i.e. $\Delta E/E<0.2$, with $\Delta E$ being the Full-width at half maximum (FWHM) of the energy resolution of the detector.

Such detector cells of lines 30 and 34 my be cadmiumtelluride or CZT based detector cells, which are both outside of the slice plane of the fan-beam 11. In other words, both energy resolving lines 30 and 34 are arranged at the gantry 1 opposite to the x-ray source 4 with an offset from the slice plane in a direction parallel to the rotational axis 2. The detector line 30 is arranged with a positive offset with respect to the direction of the rotational axis 2 depicted in FIG. 1, whereas the line 34 is arranged with a negative offset from the slice plane with respect to the direction of the rotational axis 2 depicted in FIG. 1.

The detector lines 30 and 34 are arranged at the gantry 1 such that they are parallel to the slice plane and out of the slice plane with such an offset in a positive or negative direction of the rotational axis 2 of the gantry 1, such that they receive or measure a scatter radiation scattered from the item of baggage 7 in the examination area of the computer tomograph. Thus, in the following, lines 30 and 34 will also be referred to as scatter radiation detector. It has to be noted that instead of the provision of two energy resolving lines 30 and 34, it may also be efficient to provide only one line which includes energy resolving detector elements, such as, for example, only the line 30. Furthermore, instead of providing only two energy resolving lines 30 an 34, it is also possible to provide three, four or an even greater number of energy resolving lines. Thus, if, in the following the term "scatter radiation detector" is used, it includes any detector with at least one line of energy resolving detector cells, which is arranged out of the fan plane of the fan-beam 11, such that it receives photons scattered from the item of baggage 7.

The second type of detector lines provided on the detector 8, which are indicated by a hatching, are scintillator cells. In particular, line 15 is arranged such that it is in the slice plane of the fan-beam 11 and measures the attenuation of the radiation emitted by the source of radiation 4, caused by the item of baggage 7 in the examination area. As depicted in FIG. 1, right and left of the line 15, there may be provided further detector lines including scintillator detector cells.

As already indicated with respect to the energy resolving lines 30 and 34, where the provision of only one energy resolving line 30 or 34 is sufficient, the provision of only the line 15 measuring the attenuation caused by the item of baggage 7 of the primary beam of the fan-beam 11 in the slice plane is sufficient. However, as in the case of the energy resolving lines 30 and 34, a provision of a plurality of detector lines 32, each comprising a plurality of scintillator cells, may further increase the measurement speed of the computer tomograph. In the following, the term "primary radiation detector" will be used to refer to a detector, including at least one line of scintillator or similar detector cells for measuring an attenuation of the primary radiation of the fan-beam 11.

As may be taken from FIG. 1, the detector cells of the detector 8 are arranged in lines and columns, wherein the columns are parallel to the rotational axis 2, whereas the lines are arranged in planes perpendicular to the rotational axis 2 and parallel to the slice plane of the fan-beam 11.

The apertures of the aperture systems 5 and 9 are adapted to the dimensions of the detector 8 such that the scanned area of the item of baggage 7 is within the fan-beam 11 and that the detector 8 covers the complete scanning area. Advantageously, this allows to avoid unnecessary excess radiation applied to the item of baggage 7. During a scan of the item of baggage 7, the radiation source 4, the aperture systems 5 and 9 and the detector 8 are rotated along the gantry 1 in the direction indicated with arrow 16. For rotation of the gantry 1 with the source of radiation 4, the aperture systems 5 and 9 and the detector 15, the motor 3 is connected to a motor control unit 17, which is connected to a calculation unit 18.

In FIG. 1, the item of baggage 7 is disposed on a conveyor belt 19. During the scan of the item of baggage 7, while the gantry 1 rotates around the item of baggage 7, the conveyor belt 19 displaces the item of baggage 7 along a direction parallel to the rotational axis 2 of the gantry 1. By this, the item of baggage 7 is scanned along a helical scan path. The conveyor belt 19 can also be stopped during the scans to thereby measure single slices.

The detector 8 is connected to a calculation unit 18. The calculation unit 18 receives the detection results, i.e. the readouts from the detector elements of the detector 8 and determines a scanning result on the basis of the scanning results from the detector 8, i.e. from the energy resolving lines 30 and 34 and the lines 15 and 32 for measuring the attenuation of the primary radiation of the fan-beam 11. In addition to that, the calculation unit 18 communicates with the motor control unit 17 in order to coordinate the movement of the gantry 1 with the motors 3 and 20 or with the conveyor belt 19.

The calculation unit 18 is adapted for reconstructing an image from readouts of the primary radiation detector, i.e. detector lines 15 and 32 and the scatter radiation detector, i.e. lines 30 and 34. The image generated by the calculation unit 18 may be output to a display (not shown in FIG. 1) via an interface 22.

Furthermore, the calculation unit 18 is adapted for the detection of explosives in the item of baggage 7 on the basis of the readouts of the lines 30 and 34 and 15 and 32. This can be made automatically by reconstructing scatter functions from the readouts of these detector lines and comparing them to tables including characteristic measurement values of explosives determined during preceding measurements. In case the calculation unit 18 determines that the measurement values read out from the detector 8 match with characteristic measurement values of an explosive, the calculation unit 18 automatically outputs an alarm via a loudspeaker 21.

During the subsequent description of FIGS. 2 to 7, the same reference numbers as used in FIG. 1 will be used for the same or corresponding elements.

Figure 2:
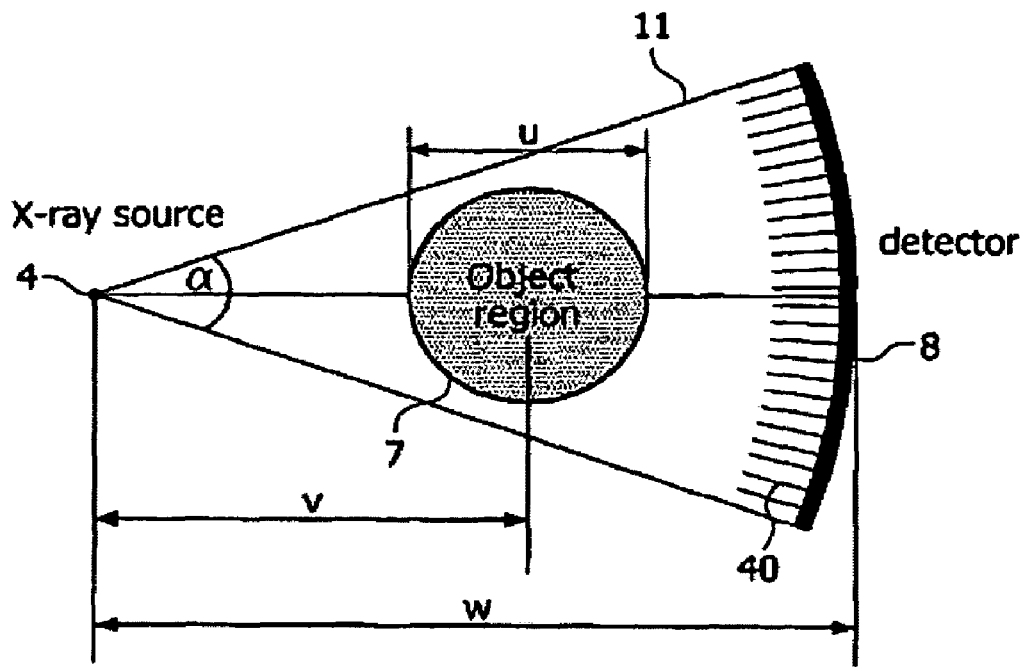
FIG. 2 shows a schematic representation of the geometry of the computer tomograph of FIG. 1 for the measurement of coherent scatter radiation.

FIG. 2 shows a simplified schematic representation of a geometry of the CSCT scanning system depicted in FIG. 1. As may be taken from FIG. 2, the x-ray source 4 emits the fan-beam 11 such that it includes the item of baggage 7 in this case having a diameter of u and covers the entire detector 8. The diameter of the object region may, for example, be 100 cm. In this case, an angle a of the fan-beam 11 may be 80°. In such an arrangement, a distance v from the x-ray source 4 to the center of the object region is approximately 80 cm and the distance of the detector 8, i.e. of the individual detector cells from the x-ray source 4 is approximately w=150 cm.

As can be taken from FIG. 2, according to an aspect of the present invention, the detector cells or lines can be provided with collimators 40 to avoid that the cells or lines measure unwanted radiation having a different scatter angle. The collimators 40 have the form of blades or lamellas, which can be focused towards the source. The spacing of the lamellas can be chosen independently from the spacing of the detector elements.

Instead of a bent detector 8 as depicted in FIGS. 1 and 2, it is also possible to use a flat detector array.

Figure 3:
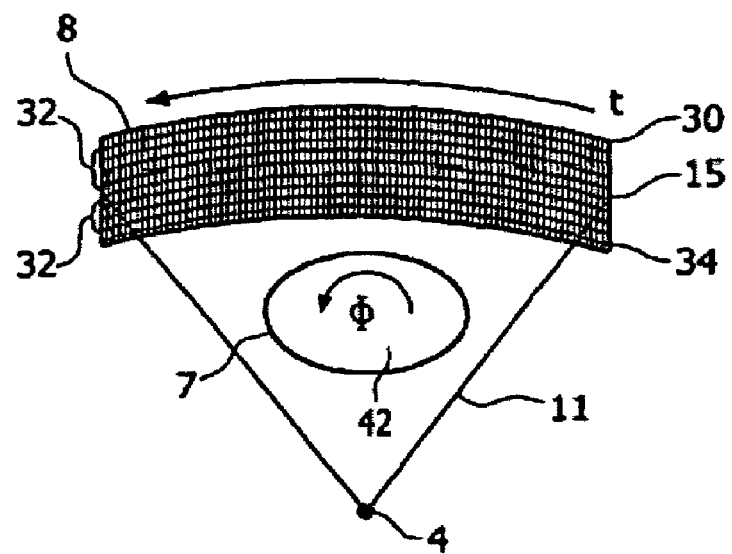
FIG. 3 shows another schematic representation of the geometry of the computer tomograph of FIG. 1.

FIG. 3 shows another schematic representation of a detector geometry as used in the computer tomograph of FIG. 1. As already described with reference to FIG. 1, the detector 8 may comprise one, two or more energy resolving detector lines 30 and 34 and a plurality of lines 15 and 32 for measuring the attenuation of the primary fan-beam caused by the item of baggage 7. As may be taken from FIG. 3, preferably the detector 8 is arranged such that one line of the lines 15 and 32, preferably the middle line 15 of the detector 8, is within the slice plane of the fan-beam 11 and thereby measures the attenuation in the primary radiation. As indicated by arrow 42, the radiation source of x-ray source 4 and the detector 8 are rotated together around the item of baggage to acquire projections from different angles.

As depicted in FIG. 3, the detector 8 comprises a plurality of columns t.

Figure 4:
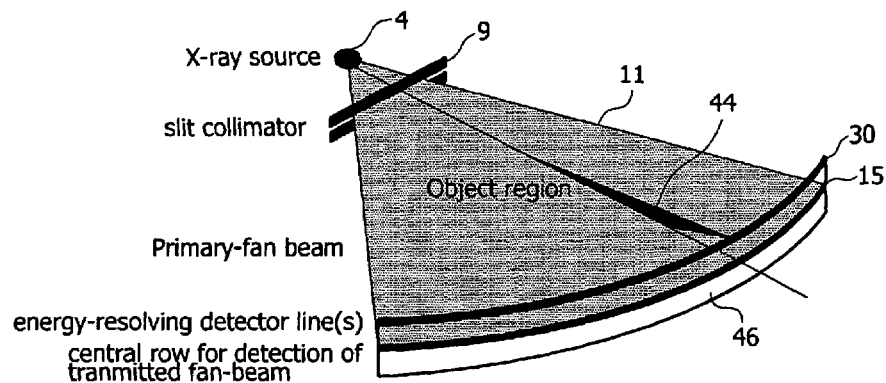
FIG. 4 shows another schematic representation of the measurement geometry of the computer tomograph of FIG. 1 for further explaining the present invention.

FIG. 4 shows another schematic representation of the geometry of the computer tomograph depicted in FIG. 1 for further explaining the present invention. In FIG. 4, a detector 46 is depicted, comprising only one line 15 and only one line 30. The line 15 is arranged in the slice plane of the fan-beam 11 formed by the aperture system 9, which in this case is a slit collimator and generated by means of the source of radiation or x-ray source 4. The line 15 comprises, for example, scintillator cells or other suitable cells for measuring the attenuation of the primary beam of the fan-beam 11 and allows for an integral measurement of the attenuation of the primary fan-beam caused by the object of interest in the object region or examination region.

Line 30 depicted in FIG. 4 includes energy resolving cells. As may be taken from FIG. 4, the line 30 is arranged parallel to the slice plane of the fan-beam 11 but out of the plane. In other words, the line 30 is arranged in a plane parallel to the slice plane and parallel to the line 15.

Reference numeral 44 indicates a scatter radiation, i.e. a photon scattered by the object of interest, such as the item of baggage. As may be taken from FIG. 4, the scatter radiation leaves the slice plane and impinges onto a detector cell of the line 30.

Figure 5:
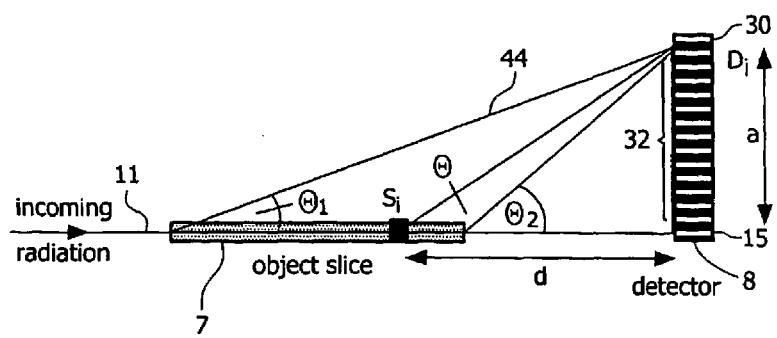
FIG. 5 shows a schematic representation of a side view of the geometry of the computer tomograph of FIG. 1.

FIG. 5 shows a side view of the detector geometry of the computer tomograph of FIG. 1. FIG. 5 can also be contemplated as showing a side view of FIG. 4, where, however, instead only the provision of one line 30 and one line 15, in FIG. 5, there is provided a plurality of detector lines 32 between the line 30 and the line 15. The detector element $D_i$ of the line 30 is an energy resolving detector element. The detector element $D_i$ is arranged with a fixed distance a from the slice plane of the primary fan-beam. According to an aspect of the present invention, for each detector element $D_i$ of the column t and for each projection $\Phi$ (see FIG. 3) a spectrum I (E, t, $\Phi$) is measured. Performing this measurement for a plurality of projections $\Phi$ along a circular or helical scan path, a three-dimensional dataset is acquired. Each object pixel is described by three coordinates (x, y, q). Thus, according to an aspect of the present invention, for reconstructing an image or for reconstructing further information from the three-dimensional dataset, a 3D→3D reconstruction method such as the one described in DE 10252662.1, which is hereby incorporated by reference.

On the basis of the spatial coordinates (x, y), a distance d of each object voxel $S_i$ to the detector 8 is calculated by means of the calculation unit 18. Then, the calculation unit 18 calculates a scatter angle θ for each object voxel $S_i$ and spaces of the following equation:

$$\theta = a\tan(a/d) \tag{Equation 1}$$

Then, on the basis of this calculation, the calculation unit 18 calculates the wave-vector transfer parameter q on the basis of the following equation:

$$q = \frac{E}{hc}\sin(\theta/2), \tag{Equation 2}$$

wherein h is the Planck's constant and c is the speed of light and E the photon energy.

Then, on the basis of the wave-vector transfer parameter q calculated in accordance with the above formula and on the basis of the readouts of the primary radiation detector, the calculation unit 18 may determine an image or may discriminate the material in the object slice.

Figure 6:
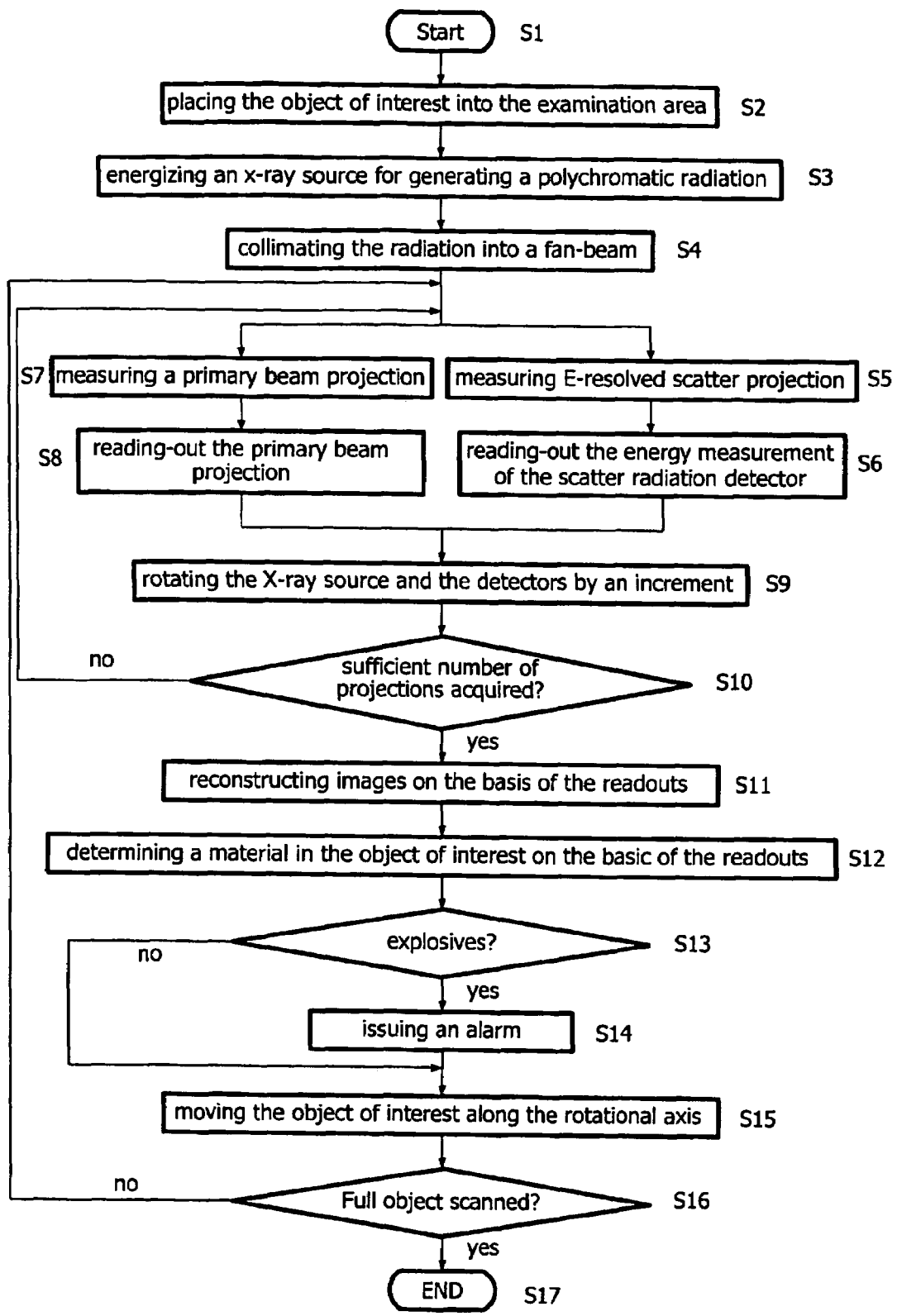
FIG. 6 shows a flow-chart of an exemplary embodiment of a method for operating the computer tomograph of FIG. 1 according to the present invention.

FIG. 6 shows a flowchart of an exemplary embodiment of a method of operating a computer tomograph of FIG. 1.

After the start in step S1, an object of interest, such as an item of baggage 7, is placed into the examination area in step S2. Then, this method continues to step S3, where the source of radiation is energized for generating a fan-beam 11 of polychromatic radiation. In the subsequent step S4, the radiation to be measured by the scatter radiation detector, i.e. by the lines 30 and 34 of the detector 8, is collimated by means of the collimator means.

Preferably, as indicated in step S4, the radiation is collimated into a fan beam. Then, the method continues to steps S5 and S7. In S5, the energy resolved scatter projection is measured by means of the energy resolving lines; i.e. lines 30 and 34 of the detector 8. In step S6, which is performed subsequent to step S5, the energy measurement of the scatter radiation detector, i.e. lines 30 and 34 is read out.

In step S7, the primary beam projection is measured by means of the primary radiation detector, i.e. lines 32 and 15. In step S8 following S7, the primary beam projections are read out. Then, in step S9, following steps S8 and S6, the x-ray source 4 and the detector 8, including the scatter radiation detector and the primary radiation detector are rotated by an increment. Then, the method continues to step S10, where it is determined whether a sufficient number of projections was acquired. In case it is determined in step S10 that further projections have to be acquired, the method returns to steps S7 and S5, such that steps S7, S8 and S5, S6 are performed parallel to each other.

In case it is determined in step S10 that a sufficient number of projections was acquired, the method continues to step S11, where images are reconstructed on the basis of the readout. The reconstruction of the images in step S11 may, for example, include the tomographic reconstruction on the basis of the ART algorithm or the filtered back projection technique (FBP).

After step S11, the method continues to step S12, where a material in the object of the interest is determined on the basis of the readouts or the reconstructed images. In case it is determined in the subsequent step S13 that the material contains explosives, the method continues to step S14, where an alarm is issued.

In case it is determined in step S13 that no explosives are contained in the object of interest, the method continues to step S15.

In step S15, the object of interest is moved along the rotational axis. Then, the method continues to step S16, where it is determined whether the full object of interest was scanned. In case it is determined in step S16 that the full object of interest has not yet been scanned, the method returns to steps S7 and S5.

In case it is determined in step S16 that the full object was scanned, the method continues to step S17, where it ends.

Advantageously, the method described with reference to FIG. 6, according to an exemplary embodiment of the present invention, is highly time efficient, since the measurement of the primary beam projections and the energy resolved scatter projections is performed at the same time.

Figure 7A:
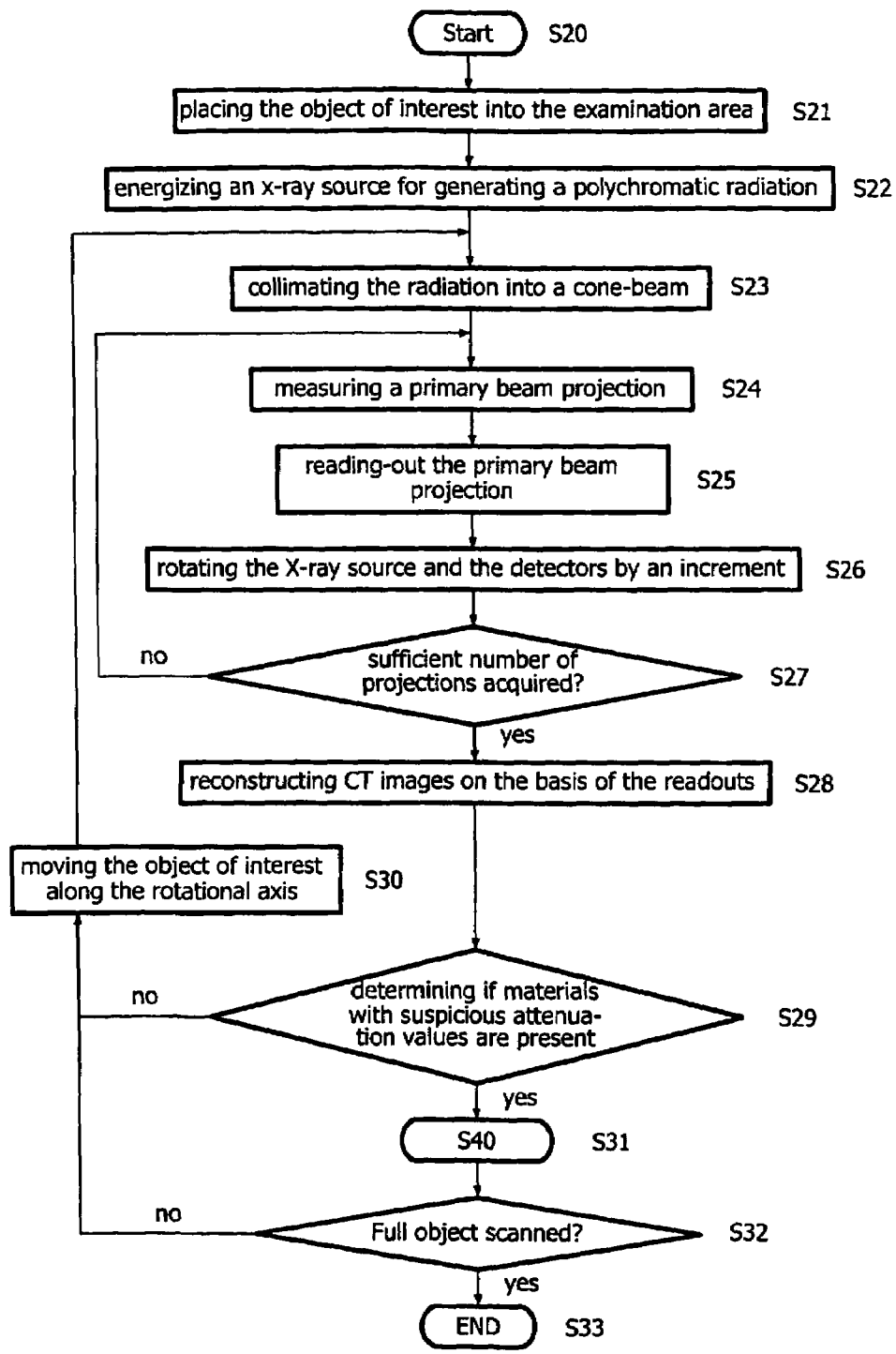
FIGS. 7a and 7b show a flow-chart of another exemplary embodiment of a method for operating the computer tomograph of FIG. 1 according to the present invention.
Figure 7B:
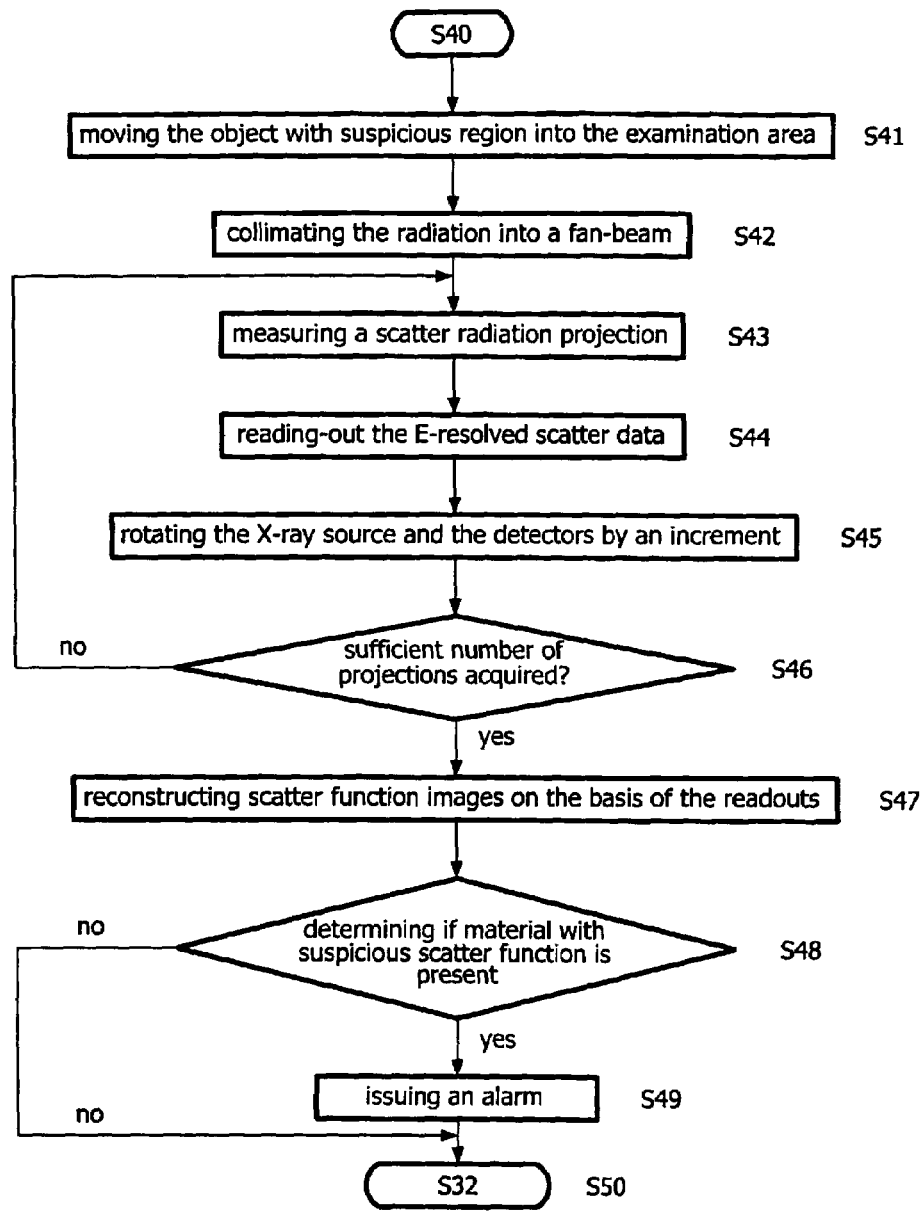

FIGS. 7a and 7b show a flowchart of another exemplary embodiment of a method for operating the computer tomograph of FIG. 1 according to the present invention.

After the start in step S20, an object of interest such as an item of baggage 7 is placed into the examination area in step S21. Then, the method continues to step S22, where the source of radiation 4 is energized for generating a polychromatic radiation. In the subsequent step S23, the radiation to be measured is collimated into a cone beam.

Then, in the subsequent step S24, a primary beam projection is measured by means of the primary radiation detector, i.e. the one or a plurality of lines 15 or 32. Then, the method continues to step S25, where the primary beam projections are read out from the primary radiation detector.

In the subsequent step S26, the x-ray source 4 and the primary radiation detector are rotated by an increment. Then, it is determined in the subsequent step S27 whether a sufficient number of projections was acquired. In case it is determined in step S27 that further projections have to be acquired, the method returns to step S24.

In case it is determined in step S27 that a sufficient number of projections was acquired, the method continues to step S28, where CT images are reconstructed on the basis of the readouts. Then, in the subsequent step S29, it is determined whether materials with suspicious attenuation values are in the object of interest. In case it is determined in step S29 that there are no suspicious materials, i.e. materials with suspicious attenuation values in the object of interest, the method continues to step S30, where the object of interest is moved along the rotational axis. Then, from step S30, the method returns to step S23.

In case it is determined in step S29 that there is a material in the object of interest which has suspicious attenuation values, the method continues to step S31, where the method jumps to step S40 in FIG. 7b. In step S41 of FIG. 7b, the object of interest is displaced such that a suspicious region containing the material with the suspicious attenuation values of the object of interest is in the examination area. Then, in the subsequent step S42, the radiation emitted by the source of radiation 4 is collimated into a fan beam. In the subsequent step S43, a scatter radiation projection is measured by means of the scatter radiation detector, i.e. lines 30 and 34 of the detector 8. As mentioned above, the scatter radiation detector preferably consists of at least one line, comprising a plurality of energy resolving detector cells. Preferably these energy resolving detector cells are direct-converting semi-conductor detectors, which directly convert the radiation into electrical charges - without scintillation. Preferably, these direct-converting semi-conductor detectors have an energy resolution better than 20% FWHM.

Then, in the subsequent step S44, the energy resolved scatter data is read out and in the subsequent step S45, the x-ray source 4 and the scatter radiation detector are rotated by an increment.

In the subsequent step S46, it is determined whether a sufficient number of projections was acquired. In case it is determined that further projections have to be acquired, the method returns to step S43. In case it is determined in step S46 that a sufficient number of projections was acquired, the method continues to step S47, where scatter function images are reconstructed on the basis of the readouts of step S44. Then, in the subsequent step S48, it is determined on the basis of the scatter function images, whether or not the material with the suspicious attenuation values is an explosive or hazardous material. Then, in case it is determined in step S48 that there is a hazardous material or an explosive in the object of interest, the method continues to step S49, where the calculation unit 18 issues an alarm via the loud speaker 21. Then, from step S49, the method continues to step S50.

In case it is determined in step S48 that there is no material with a suspicious scatter function, i.e. no hazardous or explosive material in the object of interest, the method continues to step S50, where the method jumps back to step S32 in FIG. 7a. In step S32 in FIG. 7a, it is determined whether the full object was scanned. In case it is determined that the object is not yet fully scanned, the method continues to step S20.

In case it is determined in step S32 that the full object was scanned, the method continues to step S33, where it ends.

According to an aspect of the present invention, the separation of the determination of the attenuation values and of the scatter radiation projections may be advantageous, insofar as a highly efficient method can be provided, where the measurement of the scatter radiation projection described with reference to FIG. 7b is only performed for objects of interest containing material with suspicious attenuation values. Due to this, preferably a two step baggage detection system may be provided, which allows for a highly efficient and secure scanning of the objects of interest.

Advantageously, according to the present invention, a very good and improved spectral resolution can be achieved, even with a polychromatic primary radiation emitted by a polychromatic source of radiation. Also, according to the present invention, as already mentioned above, only one energy resolving detector line may be necessary to measure the whole spectrum. In case a plurality of energy resolving detector lines are used, the q-range suitable for reconstruction can be extended. The q-range suited for reconstruction is explained in FIG. 8. Here exemplary an object diameter of 40 cm—centered around the Center of Rotation (CoR, FIG. 1, reference character 2) is assumed. Furthermore one detector line is placed 50 cm from the CoR and 20 mm off-set along the axis of rotation. From these geometrical considerations and using equation 2 it can be calculated that for all voxels in the object slice and for all rotational steps (projections) a q-range from ~0.5 nm$^{-1}$ to 1.8 nm$^{-1}$ is measured by the detector assuming further that the energy-resolved detectors measure the energy ranges 20 . . . 160 keV. If more than one detector line is used the same calculation has to be carried out for each line. The covered q-range is the sum of all individual q-range for each line. The q-ranges of the detector lines will overlap. The redundancy can advantageously increase the amount of detected photons for a given q-value, which in turn reduces the measurement time and the dose applied to the object of interest and/or the noise of the data. Dose reduction is of primary concern particular in medical applications.

The energy resolving lines 30 and 34 may, for example, be assembled from individual cadmiumtelluride (CdTe), CZT or other direct-converting semiconductor cells, which are arranged in a row.

Figure 8:
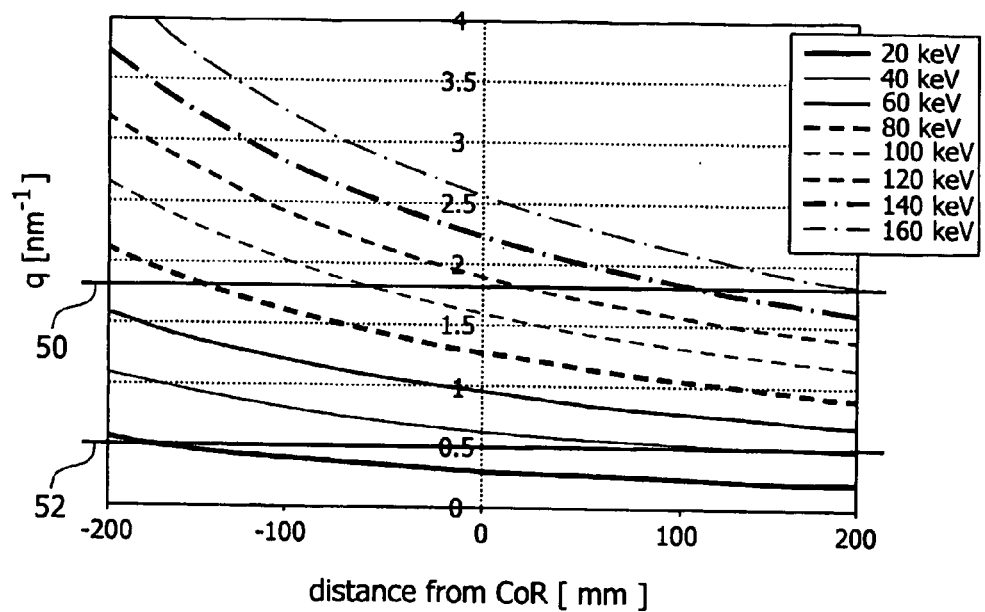
FIG. 8 shows a diagram depicting the relation of a position in the object and a wave vector amount carried over for different energies measured with the computer tomograph of FIG. 1.

FIG. 8 shows a diagram of measurements showing the relationship between a position of an object voxel $S_i$ in the object, i.e. in the item of baggage 7 and the wave vector transfer for various energies. The position of the object voxel $S^i$ is indicated by a distance from the center of rotation CoR of the gantry 1. The distance a (see FIG. 5), namely the distance of the energy resolving detector element $D^i$ to the slice plane is 20 mm and a distance between the CoR and the middles of the detector 8 is 500 mm. In other words, the detector line 30 or 34, which is energy resolving, is arranged at a distance of 20 mm from the slice plane.

Along the axis of abscissae of the diagram of FIG. 8, the distance from the CoR is mapped in millimeters and along the axis of ordinates, the wave vector transfer q, as calculated with the above formula (equation 2), is mapped in nm$^{-1}$. The various graphs in the diagram of FIG. 8 map the measurements for different energies in a range from 20 keV to 160 keV.

As can be taken from FIG. 8, in case a radiation is detected in the range from 20 to 160 keV, a complete dataset can be acquired for an object with a diameter of 400 mm for a wave vector transfer from q=0.5 . . . 1.8 nm$^{-1}$ as shown in the area between lines 50 and 52 in FIG. 8. In this range, most structures used for a material discrimination are located.

Advantageously, from the hardware point of view, except for the detector 8, a normal cone beam CT scanner or even a fan-beam scanner as known in the art may be used. For the application of the present invention, it is only necessary to provide a suitable aperture system and to add at least one energy resolving line 30 or 34 to the already existing detector.

The invention claimed is:

1. A computer tomography apparatus for examination of an object of interest, the computer tomography apparatus comprising:

a detector unit with an x-ray source and a scatter radiation detector; wherein the detector unit is rotatable around a rotational axis extending through an examination area for receiving the object of interest; wherein the x-ray source generates a fan-shaped x-ray beam adapted to penetrate the object of interest in the examination area in a slice plane; wherein the scatter radiation detector is arranged at the detector unit opposite to the x-ray source parallel to the slice plane and out of the slice plane with an offset with respect to the slice plane in a direction parallel to the rotational axis such that the scatter radiation detector is arranged for receiving a scatter radiation scattered from the object of interest; wherein the scatter radiation detector includes a first detector line with a plurality of first detector elements arranged in a line; and wherein the plurality of first detector elements are energy-resolving detector elements, the computer tomography apparatus further comprising:

a primary radiation detector, wherein the primary radiation detector includes a second detector line with a plurality of second detector elements arranged at the detector unit opposite to the x-ray source in the slice plane for receiving a primary radiation attenuated by the object of interest, wherein the second detector elements are scintillator cells; and a calculation unit for reconstructing an image from readouts of the primary radiation detector and the scatter radiation detector, wherein (i) the calculation unit, in conjunction with the primary radiation detector, is adapted to measure an attenuation of primary radiation attenuated by the object of interest, and (ii) responsive to determining that a measured attenuation of the primary radiation represents a material with suspicious attenuation values, the calculation unit is further adapted to (ii)(a) coordinate a displacement of the object of interest such that a suspicious region containing the material with suspicious attenuation values in the object of interest is in the examination area, wherein the calculation unit, in conjunction with the scatter radiation detector, is further adapted to (ii)(b) reconstruct a scatter function image and determine on the basis of the scatter function image whether or not the material with suspicious attenuation values is a suspicious medical or industrial material.

2. The computer tomography apparatus according to claim 1, wherein the energy resolving elements are direct-converting semi-conductor cells.

3. The computer tomography apparatus according to claim 1, further comprising: at least one of a plurality of first detector lines and a plurality of second detector lines; wherein at least one of the primary radiation detector and the scatter radiation detector is provided with collimator elements; and wherein the x-ray source is a polychromatic radiation source.

4. The computer tomography apparatus according to claim 1, wherein the computer tomography apparatus is adapted for detection of explosives in the object of interest on the basis of the readouts of the primary radiation detector and the scatter radiation detector.

5. A method of examining an object of interest with a computer tomography apparatus, the method comprising:

energizing an x-ray source such that the x-ray souce generates an x-ray beam which penetrates the object of interest in an examination area;

performing a measurement of primary radiation attenuated by the object of interest in a slice plane by means of a primary radiation detector that includes a detector line with a plurality of detector elements, the detector elements comprising scintillator cell;

rotating the x-ray source and the primary radiation detector around a rotational axis extending through the examination area containing the object of interest; and determining whether the measured primary radiation attenuation represents a material with suspicious attenuation values; wherein responsive to a determination that the measured primary radiation attenuation represents a material with suspicious attenuation values, the method further comprising:

coordinating a displacement of the object of interest such that the material with suspicious attenuation values in the object of interest is in the examination area, and energizing the x-ray source such that the x-ray source generates a fan-shaped x-ray beam which penetrates the object of interest in the examination area in the slice plane;

performing an integral energy measurement of a scatter radiation by means of a scatter radiation detector with a first detector line with a plurality of first energy-resolving detector elements arranged in a line;

reading-out the energy measurement from the scatter radiation detector, wherein a reconstructed scatter function image based upon the enemy measurement from the scatter radiation detector is adapted for use in determining whether or not the material with suspicious attenuation values is a suspicious medical or industrial material; and rotating the x-ray source and the scatter radiation detector around the rotational axis extending through the examination area containing the object of interest.

6. The method of claim 5, wherein the primary radiation detector is arranged opposite to the x-ray source in the slice plane.

7. The method of claim 6, further comprising the steps of: reconstructing an image from the readouts of the primary radiation detector and the scatter radiation detector; and determining whether the object of interest comprises explosives on the basis of the readouts of the primary radiation detector and the scatter radiation detector by applying reconstruction; and issuing an alarm responsive to a determination that the object of interest comprises explosives.

8. The method of claim 6, further comprising the steps of: reading out measurements of at least one of a plurality of first detector lines of the scatter radiation detector and a plurality of second detector lines of the primary radiation detector; collimating the radiation for at least one of scatter radiation detectors and the primary radiation detector; wherein the fan-shaped x-ray beam includes polychromatic radiation.

* * * * *